United States Patent [19]

Pronovost et al.

[11] Patent Number: 5,686,315
[45] Date of Patent: Nov. 11, 1997

[54] ASSAY DEVICE FOR ONE STEP DETECTION OF ANALYTE

[75] Inventors: Allan D. Pronovost, San Diego; Cathy A. Bacquet, Encinitas; Jan W. Pawlak, Cardiff-by-the Sea; Theodore T. Sand, Poway, all of Calif.

[73] Assignee: Quidel Corporation, San Diego, Calif.

[21] Appl. No.: 184,354

[22] Filed: Jan. 21, 1994

Related U.S. Application Data

[63] Continuation of Ser. No. 967,968, Oct. 27, 1992, abandoned, which is a continuation of Ser. No. 714,906, Jun. 14, 1991, abandoned.

[51] Int. Cl.$^6$ ............................................................ G01N 33/53
[52] U.S. Cl. ........................ 436/510; 435/7.92; 435/969; 435/970; 435/7.1; 436/518; 436/525; 436/527; 436/528; 436/531; 436/534; 436/805; 436/810; 436/818
[58] Field of Search ........................ 422/55–60, 101; 435/5, 67.1, 7.92, 7.2, 805, 969, 970; 436/518, 523, 525, 527, 528, 531, 533, 534, 805, 810, 814, 818

[56] References Cited

U.S. PATENT DOCUMENTS

| | | | |
|---|---|---|---|
| 4,361,537 | 11/1982 | Deutsch et al. | 422/56 |
| 4,703,017 | 10/1987 | Campbell et al. | 436/501 |
| 4,818,677 | 4/1989 | Hay-Kaufman | 435/4 |
| 4,855,240 | 8/1989 | Rosenstein et al. | 436/514 |
| 4,861,711 | 8/1989 | Friesen | 436/7 |
| 4,889,816 | 12/1989 | Davis | 436/518 |
| 4,912,034 | 3/1990 | Kalra | 435/7 |
| 4,916,056 | 4/1990 | Brown, III et al. | 435/7.9 |
| 4,920,046 | 4/1990 | McFarland | 435/7 |
| 4,943,522 | 7/1990 | Eisinger et al. | 435/7 |
| 4,956,302 | 9/1990 | Gordon | 436/161 |
| 4,960,692 | 10/1990 | Lentrichia | 435/7 |
| 4,965,047 | 10/1990 | Hammond | 422/58 |
| 4,981,786 | 1/1991 | Dafforn | 435/7 |
| 5,104,619 | 4/1992 | de Castro et al. | 422/56 |
| 5,106,758 | 4/1992 | Adler et al. | 422/58 |
| 5,110,550 | 5/1992 | Schlipfenbacher et al. | 422/57 |
| 5,120,643 | 6/1992 | Ching et al. | 435/7.92 |
| 5,122,451 | 6/1992 | Tanaka et al. | 422/57 |
| 5,130,231 | 7/1992 | Kennedy et al. | 422/56 |
| 5,141,850 | 8/1992 | Cole et al. | 422/58 |
| 5,145,789 | 9/1992 | Corti et al. | 436/530 |
| 5,160,701 | 11/1992 | Brown et al. | 422/56 |
| 5,166,051 | 11/1992 | Killeen et al. | 422/57 |
| 5,177,021 | 1/1993 | Kondo | 422/58 |
| 5,200,321 | 4/1993 | Kinwell | 422/56 |
| 5,215,886 | 6/1993 | Patel et al. | 422/56 |
| 5,217,905 | 6/1993 | Marchand et al. | 422/56 |
| 5,219,762 | 6/1993 | Katamine et al. | 422/60 |

FOREIGN PATENT DOCUMENTS 8808534  3/1988  WIPO ................ 435/970 X

*Primary Examiner*—Carol A. Spiegel
*Attorney, Agent, or Firm*—Morrison & Foerster LLP

[57] ABSTRACT

A "one step" device for the detection of analyte in clinical assays is disclosed. A visible label comprising a visible moiety and a ligand that binds to or competes with analyte is contained in a fluid conducting membrane or prefilter; and the analyte and associated ligand are conducted by the flow of sample into a detection zone. The detection zone contains a capture reagent that binds to label or to analyte bound to label.

15 Claims, No Drawings

ASSAY DEVICE FOR ONE STEP DETECTION OF ANALYTE

This application is a continuation of application Ser. No. 07/967,968, filed Oct. 27, 1992, and now abandoned, which is a continuation of application Ser. No. 07/714,906 filed Jun. 14, 1991 and now abandoned.

TECHNICAL FIELD

The invention relates to immunological and other assay methods and apparatus, especially to those for testing biological samples.

BACKGROUND ART

The literature on various forms of specific binding assays, especially immunoassays, is extensive and commercial products are numerous. A large number of simplified and conveniently packaged assays are currently available. Nonetheless, there remains a need for assay devices which are easy to use and unambiguous to interpret.

U.S. Pat. No. 4,703,017, assigned to Becton Dickinson, describes test strip devices wherein binders for an analyte and/or a visible tracer are applied to defined areas of a solid support by adsorption or covalent coupling. After application of the binder to one or more test areas of the substrate, the residual binding capacity of the test substrate is saturated or blocked by treatment with one or more types of proteins which do not specifically bind the materials to be employed in the assay. The tracer, when bound under assay conditions to the binder or to the analyte bound to the binder, is visible on the support without further treatment. The test strip is contacted and incubated with a sample containing (or suspected of containing) analyte; a sample strip may be provided with a plurality of test areas. U.S. Pat. No. 4,855,240, also assigned to Becton Dickinson, describes an assay wherein a sample and a tracer as described in U.S. Pat. No. 4,703,017 are applied at disparate locations on a flat lateral flow device.

U.S. Pat. No. 4,943,522 to Eisinger et al., the entire disclosure of which is hereby incorporated by reference, describes methods and apparatus for conducting specific binding pair assays, such as immunoassays. A porous membrane capable of non-bibulous lateral flow is used as assay substrate. A member of the binding pair is affixed in an indicator zone defined in the substrate. The sample is applied at a position distant from the indicator zone and permitted to flow laterally through the zone. Analyte in the sample is complexed by the affixed specific binding member and detected; in one preferred method of detection, entrapment of observable particles in the complex is employed.

SUMMARY OF THE INVENTION

The invention provides rapid and accurate methods for assessing the presence or absence of analytes in biological samples and devices for the conduct of these methods. In accordance with the present invention, there is provided an assay device for the detection of the presence or absence of an analyte in a sample, the assay comprising the binding of the analyte to a specific binding partner, wherein the assay device comprises a detachable fluid conducting membrane which is capable of transporting a label into, and which is in fluid communication with, a detection zone comprising a matrix containing reagent capable of capturing the label to which analyte may also be bound. The label suitably comprises visible moieties coupled to a ligand; the ligand is chosen so that it specifically binds to or competes with the analyte in the assay.

In accordance with preferred embodiments of the invention, the fluid conducting membrane contains the label which travels with the analyte. In accordance with alternative embodiments, the label is provided separately from the fluid conducting membrane; sample containing analyte is mixed with the label and the mixture then introduced into the fluid conducting membrane without washing or other treatment.

DETAILED DESCRIPTION OF THE INVENTION

The visible moieties employed in accordance with the invention are species which may be coupled to a suitable ligand for use in an assay method (e.g., specific binding partner for analyte or analyte competitor) and detected if accumulated in the detection zone. Suitable visible moieties include simple dyes or dye polymers which are visible when present in sufficient quantity, or can be (and are in many instances preferred to be) particles such as dyed latex beads, liposomes, or metallic, organic, inorganic or dye sols, dyed or colored cells or organisms, red blood cells, pigment particles and the like. Means for including various dyes within liposomes are well known, and have been disclosed, for example, in U.S. Pat. No. 4,695,554 and U.S. Pat. No. 4,703,017 as utilized in the examples below.

The visible moieties used in the assay provide the means for detection of the nature and quantity of result. Accordingly, their appearance in the detection zone must be a function of the analyte in the sample. In general, the assay is designed in a manner such that the appearance and intensity of color in the detection zone provides an easily interpreted qualitative and/or quantitative reading for the presence of analyte.

Suitable analytes to which the method of the invention can be applied are any for which a specific binding partner or competitor can be found. In general, most analytes of medical and biological significance can find specific binding partners in antibodies prepared against them or fragments of these antibodies; similarly, in most instances either additional analyte itself or an immunologically cross-reactive analog may be employed to prepare label, and thus may serve as suitable competitor. Suitable analytes include soluble analytes such as hormones, enzymes, lipoproteins, bacterial or viral antigens, immunoglobulins, lymphokines, cytokines, drugs, soluble cancer antigens, and the like. These analytes include various proteins such as protamines, histones, phosphorylated proteins, nucleoproteins, and so forth such as, for example, transcortin, erythropoietin, transferrin, various globulins, thyroxin-binding globulin, the immunoglobulins of various subclasses A, G, D, E, and M, various complement factors, blood clotting factors such as fibrinogen, Factor VIII, tissue thromboplastin, and thrombin.

Also included are hormones such as insulin, glucagon, relaxin, thyrotropin, somatotropin, gonadotropin, follicle-stimulating hormone, gastrin, bradykinin, vasopressin, and various releasing factors. A wide range of antigenic polysaccharides, lipopolysaccharides, lipoproteins, proteoglycans and glycoproteins can also be determined such as those from Chlamydia, *Neisseria gonorrheae, Pasteurella pestis, Shigella dysentereae,* and certain fungi such as Mycosporum and Aspergillus. Yet another major group comprises oligonucleotide sequences which react specifically with other oligonucleotides or protein targets. Extensive lists and discussions of soluble analytes determinable in the method of the invention are found in the aforementioned U.S. Pat. No. 4,943,522 and in U.S. Pat. No. 3,996,345, which is incorporated herein by reference.

As is well known to those of skill in the art, a wide variety of possible assay strategies are available, depending primarily on the nature of the analyte and the availability of suitable reagents for use in the assay. The experimental design protocol of the assays may therefore be varied as is generally known for assays based on specific binding. In particular, most of the protocols adapted to other physical formats of immunoassay can be used in the apparatus of the invention, where the detection zone fills the role of the binding member (e.g., antibody or antigen) bound to a solid support. Thus, suitable binding pairs for use in accordance with the invention include, but are not limited to, the following types of interacting components: antigen/antibody; antibody/hapten; antibody/cell or cell fragment; RNA/DNA probes; receptor/receptor ligands; enzyme/substrate; enzyme/inhibitor and lectin/carbohydrate.

Where the analyte itself provides a visible moiety, or such moiety may be directly associated with the analyte prior to its introduction into the assay device, direct interaction of analyte labeled by the associated visible moiety with its binding complement may be carried out in the detection zone using detection reagent specific for the analyte. Most typically, however, assays in accordance with the present invention are directed to the detection of analytes which do not contain a visible moiety and do not readily permit direct association of the visible moiety per se thereto. The prefilter may also facilitate blood separation for whole blood samples by filtration, adsorption or specific binding or capture. For determination of the presence of such analytes, the assays are carried out pursuant to one of the following strategies: coupling the visible moieties to a ligand which binds specifically to analyte; coupling the visible moieties to a ligand which binds an intermediary agent binding the analyte; and coupling the visible moieties to a ligand which competes with analyte for a detection reagent in the detection zone. Depending on the nature of the analyte, a competitive inhibition assay protocol might also be suitable.

For preparation of analyte binding label, the visible moieties are coupled to a particular binding partner which binds the analyte specifically. For example, if the analyte is an antigen, an antibody specific for this antigen (or immunologically reactive fragments of the antibody, such as F(ab')$_2$, Fab or Fab') would be a suitable ligand for preparation of an analyte binding label specific thereto. These visible moieties, or "test" visible moieties, form complexes with any analyte in the sample when the sample is brought into contact with the label, either prior to introduction of the entire sample into the test device or as the sample passes through the labeling zone. Analyte/label complexes (as well as any unbound materials) are carried into the detection zone by the liquid flow. When the complexes reach the detection zone, a capture reagent specific for analyte (such as an antibody or fragment thereof as set forth above) retains those coupled conjugates to which analyte has been bound; label which is not associated with analyte passes therethrough or is washed therefrom.

As such a method employs capture agent and label both specific for analyte, it is generally appropriate to use an excess of label; in this manner, the probability that all analyte in a sample is bound to label prior to its introduction into the capture zone is greatest, while any complexed label is readily removed by washing. Because both the ligand of the label and the capture reagent are specific for the analyte, it is necessary to select ligand and capture agent directed to different, non-overlapping binding sites on the analyte; for example, when the analyte is a polypeptide, the ligand and the capture agent may suitably each be monoclonal antibodies immunospecific for different, non-overlapping epitopes of the polypeptide.

Indirect detection methods involve use of a labeled secondary reagent to detect the presence of a bound analyte (or binding partner therefor). Thus, for example, the presence of bound antibodies in the detection zone could be evaluated using labeled anti-immunoglobulin antibodies, protein A or protein G. Similarly, in some instances the analyte/label complex may be bound to the detection reagent via the label, rather than the analyte; as an example, when binding of analyte to a protein ligand induces a conformational change in the ligand, binding of ligand to detection reagent which would otherwise not occur may be possible. A particular advantage in the use of indirect detection methods is that a single labeled preparation of, e.g., anti-IgG antibodies could be used to detect a wide variety of different bound analyte/IgG complexes.

Competitive approaches (either binding or inhibition) call for the use of ligand which has at least one significant assay-related property in common with the analyte. For example, in the competitive binding approach the visible moieties are coupled to a ligand which is competitive with analyte for a capture reagent in the detection zone; most typically, other molecules of the analyte itself are used as competitor. Both the analyte from the sample and the competitor bound to the visible moieties are then carried into the detection zone. While analyte and its competitor both react with the detection reagent (which most typically is specifically reactive with both analyte and its competitor), the unlabeled analyte is able to reduce the quantity of competitor-conjugated visible moieties which are retained in the detection zone. This reduction in retention of the visible moieties becomes a measure of the analyte in the sample.

In accordance with one preferred embodiment of the invention, the detachable fluid conducting membrane is provided with the label included therein. Suitably, the label is present in the membrane in lyophilized form. In accordance with this embodiment, the sample to be tested is introduced into the test device and contact between analyte and label is made in the membrane. In accordance with alternative embodiments, however, the sample may be contacted with the label prior to introduction into the test device; for example, the sample to be tested may be added directly to a pre-measured portion of label and the mixture then introduced into the test device.

The detection zone comprises a matrix containing reagent capable of appropriate interaction with the label. The detection reagent is affixed physically, chemically, biologically or otherwise to the matrix of the detection zone in a manner such that label introduced into the zone is captured when it is associated with the appropriate binding partner and allowed to pass through the zone when it is not so associated. It is not necessary that the detection reagent be bound directly to the matrix; for example, the detection reagent may be attached to another material which in turn is physically entrapped in the detection zone or otherwise affixed thereto. For example, a detection reagent may be attached covalently or passively to beads or the like, and the beads then affixed on the membrane. It is important, however, that the detection reagent not be removed from the detection zone when the test device is subjected to whatever treatments are appropriate to remove unbound materials therefrom. Appropriate methods to affix suitable detection agents to the matrix of the detection zone are well known in the art, and therefore form no part of the present invention.

The fluid conducting membrane may also include (or the label may be provided with) "control" visible moieties which do not contain the specific binding agent or analyte competitor and which are also carried through to a control area of the detection zone by the liquid flow. These control visible moieties are coupled to a control reagent which binds to a capture partner specific for it and can then be captured in a "control" portion of the detection zone to verify that the flow of liquid is as expected. The visible moieties used in the control may be the same or different color than those used for the test moieties. If different colors are used, ease of reading the results is enhanced.

The following examples are intended to illustrate but not to limit the invention.

EXAMPLE 1

Preparation of a Labeled-Bead, One-Step Assay Device for Human Chorionic Gonadotropin (hCG)

The test device has two principal components—a solid phase subassembly and a prefilter assembly. The components, which communicate through liquid flow, are assembled so as to support the active components of the device. The construction is as follows.

Preparation of the Solid Phase Subassembly

The solid phase subassembly in this embodiment comprises a plastic insert placed into a molded bottom casing. An absorbent assembly, which in preferred embodiments comprises a plurality of absorbent layers, was placed on the plastic insert. A particularly suitable absorbent assembly pad is composed of a plurality of layers of filtration media comprising Quidel #9117 absorbent assembly (as available, for example, under the indicated trade designations: 0.6μ polycarbonate (Nucleopore), 5S rayon, 593, #300 and #300 (all from Schleicher and Schuell), sewn together in the order indicated.

On top of the adsorbent assembly was a nitrocellulose membrane having a triangular detection zone and a bar "control" zone thereon. The triangular detection zone was generated by using a triangle template and vacuum suction through the nitrocellulose membrane of 500 μl of rabbit anti-hCG antibody purified using Protein A from rabbit serum after two consecutive 0–33% saturated ammonium sulfate precipitations. The concentration of rabbit hCG antibody was 0.016 mg/ml in 20% glycerol, 0.1M sodium phosphate, 0.02% $NaN_3$, 0.00007% Texas Red (pH 7.0). The "control" bar was produced by using a bar template and vacuum suction through the nitrocellulose membrane of 500 μl of 2 μg/ml rabbit anti-mouse antibody (available from Jackson Laboratories), pH 7.0 in 20% glycerol, 0.1M sodium phosphate, 0.02% $NaN_3$, 0.002% Rhodamine 123 (pH 7.0). The membrane was dried for 10–20 minutes at room temperature, then soaked in 1.0% methylated bovine serum albumin (mBSA), 10% sucrose, 2.5% BSA, 0.02% $NaN_3$ and 50 mM Tris (pH 8.0) for 30 minutes. The membrane was then dried in a 45° C. oven for about 30 minutes.

A molded top casing was placed upon the treated and cut nitrocellulose, with the spotted zone in the center of the visually exposed area. The subassembly components were then sonically welded. The welded subassembly unit may be advantageously packaged for storage purposes in a heat-sealed foil pouch with a suitable desiccant.

Preparation of the Prefilter Assembly

To prepare the labeled beads for inclusion in the labeling zone, 0.5 ml of red polystyrene 0.51 micron diameter beads were washed three times with phosphate-buffered saline (PBS) (10 mM sodium phosphate, 10 g/l NaCl, 0.2% $NaN_3$, pH 7.2) by centrifugation for 8 minutes, with removal of supernatant between washes. To the final washed pellet of beads, 500 μl of a solution containing 0.38 mg/ml mouse anti-hCG and 0.13 mg/ml bovine serum albumin (BSA) in glycine-buffered saline (GBS), pH 7.2 was added. The GBS was prepared by adding 7.3 g glycine and 10 g NaCl to 1 liter water. The suspended beads were then rotated or rocked overnight at room temperature.

The beads were centrifuged and resuspended in 1 ml of a bead blocking buffer comprising 0.1M $NaPO_4$, 1% BSA and 0.02% $NaN_3$, pH 7.2. The bead preparation was then rocked or rotated for four hours at room temperature and washed three times as previously described with the bead blocking buffer. The final bead preparations were prepared by resuspending the beads (in bead blocking buffer diluted 10-fold in water) at concentrations of 2.5% bead solids and 1% bead solids, respectively.

To prepare the unit for final assembly, the prefilter subassembly comprised of 5S rayon (Schleicher and Schuell) and ED141 glass fiber (ED Scientific Specialties, Inc.) was spotted with 50 μl of 1% casein in 100 mM Tris, pH 8 and dried overnight at room temperature. To each prefilter, 20 μl of one of the bead solids preparations was added and the filter was then frozen at –70° C. and lyophilized using a Virtis Model #12 lyophilization unit. The filters were then ready for insertion into the test device.

Test Procedure

Samples (1 ml) in PBS containing either no hCG or 842 mIU/ml hCG (2nd IS) were added to prefilters prepared from either 1.0 or 2.5% bead solids solutions. The prefilters were then removed and the results evaluated. In addition to a determination of the results by the operator based upon appearance (visual call), the samples were evaluated in the areas of the triangle and bar zones in terms of Gretag density units. The results are reported in Table 1.

TABLE 1

| % Solids | mIU/ml hCG | Gretag Density Units of Triangle | Visual Call | Gretag Density Units of Negative Bar |
|---|---|---|---|---|
| 1.0 | 0 (PBS) | 0.12 | | 0.20 |
|  |  | 0.11 | – | 0.14 |
|  |  | 0.12 | – | 0.17 |
|  | 842 | 0.30 | + | 0.30 |
|  |  | 0.39 | + | 0.41 |
| 2.5 | 0 (PBS) | 0.33 | – | 0.48 |
|  |  | 0.37 | – | 0.56 |
|  | 842 | 0.47 | + | 0.60 |
|  |  | 0.49 | + | 0.54 |
|  |  | 0.44 | + | 0.57 |

EXAMPLE 2

Preparation of a Liposome-Based Device

In a manner analogous to that set forth in Example 1, a counterpart liposome-containing device was prepared. The solid phase subassembly as previously described was provided with the same adsorbent assembly #9117 as described earlier. A nitrocellulose membrane prepared in the manner described hereinafter was then placed on the adsorbent assembly.

By analogy to the procedure described in Example 1, the triangular detection zone was spotted with 500 μl of rabbit anti-hCG antibody which has been Protein A purified from rabbit serum after two consecutive 0–33% saturated ammonium sulfate precipitations. The concentration of rabbit anti-hCG antibody was 0.016 mg/ml in 20% glycerol, 0.02% NaN$_3$, 0.00007% Texas Red (pH 7.0). The bar control zone was spotted with 500 μl of crude hCG which has been purified from resuspended lyophilized pregnant urine by gel filtration. The activity of hCG was 1900 mIU/ml (2nd IS standard) in 20% glycerol, 0.1M sodium phosphate, 0.02% NaN$_3$, 0.002% Rhodamine 123 (pH=7.0). The membrane was dried for 10–20 minutes at room temperature, then blocked by soaking for 30 minutes in 1.0% methylated bovine serum albumin (mBSA), 10% sucrose, 2.5% bovine serum albumin, 0.025% NaN$_3$, 50 mm Tris (pH=8.0). The membrane was dried in a 45° C. oven for 10–20 minutes. A molded top casing was then placed on the treated nitrocellulose with the spotted zone in the center of the visual area, sonically welded and stored as in Example 1.

Liposomes conjugated to monoclonal anti-hCG, which has been purified from ascites, were prepared as follows. Ascites were 0–50% saturated ammonium sulfate (SAS) precipitated, resuspended and buffer exchanged by G-25 Fine Sephadax® gel filtration chromatography. The antibodies were then further purified using ion exchange chromatography (Q-Sepharose Fast Flow® resin with a sodium chloride gradient).

The purified antibody was diluted to 3 mg/ml in 0.1M sodium phosphate, 0.02% NaN$_3$ (pH=7.8). 8.5 molar equivalents of SPDP were added and unreacted reagents removed by gel filtration chromatography using G25 Fine Sephadex resin. Sulfhydryl groups on the antibody were released by exposure to dithiothreitol (DTT) in 0.1M sodium acetate (pH=4.5); unreacted reagents were again removed by gel filtration chromatography (G25 Fine Sephadex resin). Liposome reagent (A$_{565}$=100) containing Rhodamine prepared in accordance with U.S. Pat. No. 4,703,017 was reacted with the antibody at a ratio of 1 mg antibody/ml liposome reagent. After 2 hours, the reaction was terminated by gel filtration chromatography using 6FF Sepharose resin equilibrated in a liposome storage buffer comprising 1.3% glycerol, 0.0005% dimethyl sulfoxide, 0.1% NaN$_3$, 0.74% disodium ethylenediamine tetraacetate, 0.6% BSA, 0.1M sodium phosphate (pH=7.5). For use, the anti-hCG liposome conjugate was diluted to A$_{565}$=25 in liposome storage buffer.

To prepare the prefilter assembly, a 1 cm diameter glass fiber disk (Eaton-Dickman Scientific Specialties) and a 1 cm diameter top layer disk of 5S non-woven rayon (Schleicher and Schuell) were inserted into the prefilter retainer by pressing the disks into position and sonic welding. One hundred microliters of the hCG liposome conjugate (A$_{565}$=25) with 3% mannitol was aliquoted into the prefilter assembly and frozen in a lyophilization flask on dry ice for at least one hour. The prefilters were then lyophilized for at least twelve hours. The lyophilized prefilters were placed into the prefilter assembly for use.

Samples were prepared by adding to 1 ml of female urine various quantities of hCG as indicated below; 1 ml of urine from a pregnant female was also used. The results of application of the samples to the devices (both by operator evaluation based on appearance and by determination of Gretag value) are reported in Table 2.

TABLE 2

| HCG Spiked Urine Samples (mIU/ml, 2nd IS) | Visual Call +/− | Gretag Value |
|---|---|---|
| 0 | − | 0.26/0.27 |
| 100 | + | 0.41 |
| 200 | + | 0.49 |
| 500 | + | 0.43/0.51 |
| Pregnant | + | 0.48 |

We claim:

1. An assay device for one-step detection of the presence or absence of an analyte in a sample, wherein said device comprises:

a) a removable fluid-conducting membrane, to which the sample is applied, containing a mobilizable label, which label comprises a visible moiety coupled to a ligand which ligand specifically binds said analyte or competes with said analyte for a specific binding partner to the analyte, said membrane being in fluid communication with and on top of b) a matrix containing a first detection zone wherein said detection zone contains immobilized thereon said specific binding partner to the analyte, said matrix being in fluid communication with and on top of c) an absorbent capable of drawing liquids applied to said device through said membrane and said matrix.

2. The device of claim 1 wherein the ligand is a specific binding partner of the analyte.

3. The device of claim 2 wherein the ligand is an antibody or immunologically reactive fragment thereof.

4. The device of claim 1 wherein the ligand is a competitor with the analyte.

5. The device of claim 1 wherein the ligand is additional analyte that competes with said analyte in said detection zone.

6. The device of claim 1 wherein the specific binding partner to the analyte is an antibody or immunologically reactive fragment thereof.

7. The device of claim 1 wherein said visible moiety is a colored latex bead.

8. The device of claim 1 wherein said visible moiety is a liposome containing dye.

9. The device of claim 1 wherein said matrix further contains a second detection zone in the form of a spatially distinct positive control zone underneath the removable fluid conducting membrane comprising an immobilized detection reagent to act as a positive control which is capable of binding said label in the absence of said analyte.

10. The device of claim 9 wherein said second detection zone contains an immobilized specific binding partner for said ligand.

11. The device of claim 1, wherein said detection zone further contains immobilized thereon a control binding partner and wherein said fluid-conducting membrane further comprises a mobilizable control visible moiety that does not contain said ligand and is coupled to a control reagent that is capable of being captured by said control binding partner in said detection zone.

12. The device of claim 11, wherein said control visible moiety is coupled to said ligand in part a) of claim 1.

13. A method to detect the presence or absence of said analyte in a sample, which method comprises contacting the fluid-conducting membrane of the assay device of claim 1 with the sample so that the sample passes through the fluid-conducting membrane as defined in part a), mobilizing the label, and through the matrix of part b) and into the absorbent of part c);

removing the membrane; and observing the binding of the label in said first detection zone as a function of the presence or absence of analyte.

14. The method of claim 13 wherein said analyte is human chorionic gonadotropin (hCG).

15. The method of claim 14 wherein the specific binding partner for analyte is a monoclonal antibody immunoreactive to hCG.

* * * * *